US 8,716,383 B2

(12) United States Patent
Millet et al.

(10) Patent No.: US 8,716,383 B2
(45) Date of Patent: *May 6, 2014

(54) MATERIAL FOR THE PREVENTION OF BEDSORES

(75) Inventors: Damien Millet, Valence (FR); Eric Jourdan, Voreppe (FR)

(73) Assignee: Millet Innovation, Loriol sur Drome (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/205,680

(22) Filed: Aug. 9, 2011

(65) Prior Publication Data

US 2012/0028021 A1 Feb. 2, 2012

Related U.S. Application Data

(63) Continuation of application No. PCT/FR2010/000116, filed on Feb. 12, 2010.

(30) Foreign Application Priority Data

Feb. 13, 2009 (FR) ...................................... 09 00664

(51) Int. Cl.
*C08K 9/06* (2006.01)
(52) U.S. Cl.
USPC ............ 524/268; 524/588; 523/212; 523/105
(58) Field of Classification Search
None
See application file for complete search history.

(56) References Cited

U.S. PATENT DOCUMENTS 3,884,866 A * 5/1975 Jeram et al. ................. 523/203
3,957,713 A * 5/1976 Jeram et al. ................. 524/703
4,072,635 A * 2/1978 Jeram ......................... 523/218
5,886,111 A * 3/1999 Chiotis et al. ............... 525/478
6,169,155 B1 * 1/2001 Alvarez et al. ............... 528/15
6,972,313 B2 * 12/2005 Howe et al. .................. 528/15

FOREIGN PATENT DOCUMENTS

| CN | 1748758 A | 3/2006 |
| FR | 2712487 A1 | 5/1995 |
| WO | 0217840 A1 | 3/2002 |

OTHER PUBLICATIONS

Int'l Preliminary Report on Patentability issued Aug. 16, 2011 in Int'l Application No. PCT/FR2010/000116; Written Opinion.
Int'l Search Report issued Sep. 28, 2010 in Int'l Application No. PCT/FR2010/000116; Written Opinion.

* cited by examiner

*Primary Examiner* — Margaret Moore
(74) *Attorney, Agent, or Firm* — Panitch Schwarze Belisario & Nadel LLP

(57) ABSTRACT

A method for manufacturing a protective layer for protecting skin and tissues in a vicinity of the skin includes the steps of: forming a mixture comprising approximately 15% of dimethyl-vinyl-terminated polydimethylsiloxane with a viscosity greater than 20,000 mPa·s, approximately 25% of dimethyl-vinyl-terminated polydimethylsiloxane with a viscosity between 200 and 20,000 mPa·s, approximately 45% of trimethyl-terminated polydimethylsiloxane, approximately 12% of trimethylsiloxy-treated pyrogenic silica, and approximately 3% of dimethyl-hydrogen-terminated co-polydimethylsiloxane-polymethyl-hydrogen-siloxane; polymerizing at least partially the mixture to obtain a polymer gel; and forming the protective layer using the polymer gel. The polymer gel has, at a temperature of 35° C. and when a shearing rate varies between 0 and 100 rad/s, a shear storage modulus or elastic component varying from 11,000 to 20,000 Pa, a shear loss modulus or viscous component varying from 700 to 8,000 Pa, and a Tan Delta varying from 0.06 to 0.38.

13 Claims, 3 Drawing Sheets

MATERIAL FOR THE PREVENTION OF BEDSORES

CROSS-REFERENCE TO RELATED APPLICATIONS

This application is a Continuation of International Application No. PCT/FR2010/000116, filed Feb. 12, 2010, which was published in the French language on Aug. 19, 2010, under International Publication No. WO 2010/092259 A2 and the disclosure of which is incorporated herein by reference.

BACKGROUND OF THE INVENTION

A preferred embodiment of the present invention relates to a material particularly for the prevention of bedsores.

Various means such as creams, pads and soft materials have been used to try to prevent the formation of bedsores. However, none of these means has proven to be truly efficient.

One well-known method also involves using polymer gel-based plates, such as silicone gel or hydrogel-based plates, to protect skin or for load distribution. For example, to ensure a load distribution function, one well-known method involves using a plate made of a relatively hard silicone gel of PDMS (polydimethylsiloxane) type. Patent No. FR2712487 describes a silicone gel having properties similar to those of the footpad for the prevention of pathologies caused by hyper pressure appearing essentially on or under the feet.

However, the formation of bedsores results from stresses exerted on the tissues that differ from hyper pressures. FIGS. 1 and 2 schematically represent in a cross-section an area of skin and tissues 1 around a bone 2 bearing on a rigid surface 10. In FIG. 1, the bone 2 is separated from the rigid surface 10 by a layer of tissues of minimum thickness 1. The pressure exerted on the rigid surface leads to the formation of a stress field represented in shading 3, the grey level of which is representative of the intensity of the stresses. The darkest area located between the bone 2 and the rigid surface delimits the area in which the bearing stresses are the highest.

The tissues are therefore more compressed in line with the bone 2, and less and less compressed moving away from the bone.

In reality, the pressure of a bone is not necessarily perpendicular to the bearing surface. The phenomena occurring in this situation are shown by FIG. 2. The stress F exerted by the bone comprises a vertical component Fv and a horizontal component Fh. The vertical component can create hyper pressure and form an area 5 reducing the thickness of the skin on one side of the bone. The reduction induces poor irrigation of the tissues in this area. The horizontal component Fh induces a shear stress Fa and compression stress Fc in the tissues on either side of the bone 2, which tend to put strain on the tissues particularly due to friction on the bearing surface 10. The vessels also undergo these stresses. The skin and the deeper tissues are thus poorly irrigated due to the compression, and undergo alternate stresses parallel to the bearing surface the effects of which are all the more negative when the tissues are less elastic as is the case in elderly people or malnourished people. On the surface of the skin, this friction can also lead to the formation of lesions. The compression, shear and friction stresses thus tend to form a bedsore.

It is therefore desirable to develop a material to be placed between the skin and the bearing surface which enables the negative effects of pressure and friction on the skin to be removed, or at least reduced.

Patent application WO 02/17840 describes a dressing intended particularly for the treatment of bedsores. The dressing is made of an extensible, flexible textile material, which holds in place on the injured area of the body a pad made of a molded silicone polymer gel and having a Shore A hardness from 6 to 8. It transpires that this pad does not prevent the formation of bedsores.

BRIEF SUMMARY OF THE INVENTION

Some preferred embodiments of the present invention concern a method for manufacturing a protective layer for the skin and the tissues in the vicinity of the skin. It will be understood by one of ordinary skill in the art that, unless otherwise indicated, all viscosities described herein are measured at room temperature or 20° C.-25° C. It will also be understood by one of ordinary skill in the art that, unless otherwise indicated, all percentages described herein are in percent by weight (i.e., wt. %). According to a preferred embodiment, the method comprises the steps of forming a mixture, polymerizing at least partially the mixture to obtain a polymer gel, and forming a protective layer using the polymer gel. The mixture comprises:

approximately 15% of dimethyl-vinyl-terminated polydimethylsiloxane with a viscosity greater than 20,000 mPa·s, approximately 25% of dimethyl-vinyl-terminated polydimethylsiloxane with a viscosity between 200 and 20,000 mPa·s, approximately 45% of trimethyl-terminated polydimethylsiloxane, approximately 12% of trimethylsiloxy-treated pyrogenic silica, and approximately 3% of dimethyl-hydrogen-terminated co-polydimethylsiloxane-polymethyl-hydrogen-siloxane. The polymer gel has, at 35° C., when a shearing rate varies between 0 and 100 radians per second (rad/s), a rigidity or elastic component varying from 11,000 to 20,000 Pa, a viscous or resiliency component varying from 700 to 8,000 Pa, and a resiliency factor or Tan Delta varying from 0.06 to 0.38.

According to one preferred embodiment, the protective layer has an adhesiveness between 100 and 115 g/cm$^2$.

According to one preferred embodiment, the protective layer has a thickness between 1 and 4 mm.

According to one preferred embodiment, a face of the protective layer has asperities the diameter of which is between 2 and 20 μm.

According to one preferred embodiment, the approximately 45% of trimethyl-terminated polydimethylsiloxane has a viscosity lower than 100 mPa·s.

According to one preferred embodiment, the approximately 45% of trimethyl-terminated polydimethylsiloxane has about $\frac{3}{5}^{ths}$ of polydimethylsiloxane with a viscosity lower than 100 mPa·s, and about $\frac{2}{5}^{ths}$ of polydimethylsiloxane with a viscosity greater than 20,000 mPa·s.

According to one preferred embodiment, the polymerization is performed in the presence of platinum vinylsiloxane complex.

Some preferred embodiments also relate to a protective layer for protecting the skin and tissues in the vicinity of the skin, comprising a polymer gel obtained by polymerizing at least partially a mixture comprising:

approximately 15% of dimethyl-vinyl-terminated polydimethylsiloxane with a viscosity greater than 20,000 mPa·s, approximately 25% of dimethyl-vinyl-terminated polydimethylsiloxane with a viscosity between 200 and 20,000 mPa·s, approximately 45% of trimethyl-terminated polydimethylsiloxane, approximately 12% of trimethylsiloxy-treated pyrogenic silica, and approximately 3% of dimethyl-hydrogen terminated co-polydimethylsiloxane-polymethyl-hydrogen-siloxane, the polymer gel having at 35° C., when a shearing rate varies between 0 and 100 rad/s, a rigidity or elastic component varying from 11,000 to 20,000 Pa, a viscous or resiliency component varying from 700 to 8,000 Pa and a resiliency factor or Tan Delta varying from 0.06 to 0.38.

According to one preferred embodiment, the protective layer has an adhesiveness between 100 and 115 g/cm$^2$.

According to one preferred embodiment, the protective layer has a thickness between 2 and 3 mm.

According to one preferred embodiment, the protective layer comprises a face having asperities, the diameter of which is between 2 and 20 μm.

According to one preferred embodiment, the approximately 45% of trimethyl-terminated polydimethylsiloxane have a viscosity lower than 100 mPa·s.

According to one preferred embodiment, the approximately 45% of trimethyl-terminated polydimethylsiloxane comprises about ⅝$^{ths}$ of polydimethylsiloxane with a viscosity lower than 100 mPa·s, and about ⅜$^{ths}$ of polydimethylsiloxane with a viscosity greater than 20,000 mPa·s.

According to one preferred embodiment, the polymerization is performed in the presence of platinum vinylsiloxane complex.

Some preferred embodiments may also relate to a product for restoring or strengthening the vasodilatation reflex of skin blood capillaries, induced by applying local pressure, comprising a protective layer as defined above.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

Some examples of embodiments of the present invention will be described below in relation with, but not limited to, the following figures, in which in the drawings.

DETAILED DESCRIPTION OF THE INVENTION

Figure 3:
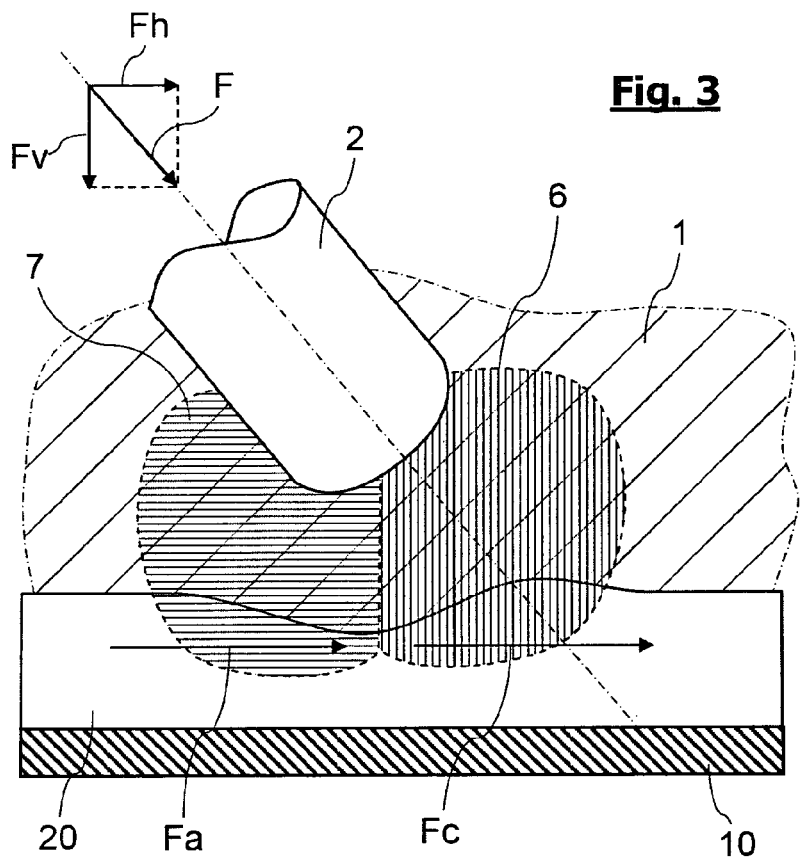
FIG. 3 is a schematic cross-section of an area of skin and tissues around a bone, covered by a protective layer made of a material according to one preferred embodiment of the present invention.

FIG. 3 represents an area of skin and tissues in the vicinity of a bone protected by a protective layer 20 according to one preferred embodiment. The protective layer 20 comprises a silicone gel obtained by polymerizing at least partially one or other of two mixtures, the content of which is described in Table 1 below:

TABLE 1

| Component | Mixture 1 | Mixture 2 |
|---|---|---|
| dimethyl-vinyl-terminated polydimethylsiloxane with a viscosity greater than 20,000 mPa · s | approx. 15% | approx. 15% |
| dimethyl-vinyl-terminated polydimethylsiloxane with a viscosity between 200 and 20,000 mPa · s | approx. 25% | approx. 25% |
| Trimethyl-terminated polydimethylsiloxane with a viscosity lower than 100 mPa · s | approx. 45% | approx. 25% |
| Trimethyl-terminated polydimethylsiloxane with a viscosity greater than 20,000 mPa · s | 0 | approx. 20% |
| Trimethylsiloxy-treated pyrogenic silica | approx. 12% | approx. 12% |
| Dimethyl-hydrogen-terminated co-polydimethylsiloxane-polymethyl-hydrogen-siloxane | approx. 3% | approx. 3% |

The partial polymerization of the Mixtures 1 and 2 is obtained using a platinum-vinyl siloxane complex catalyst.

Figure 4:
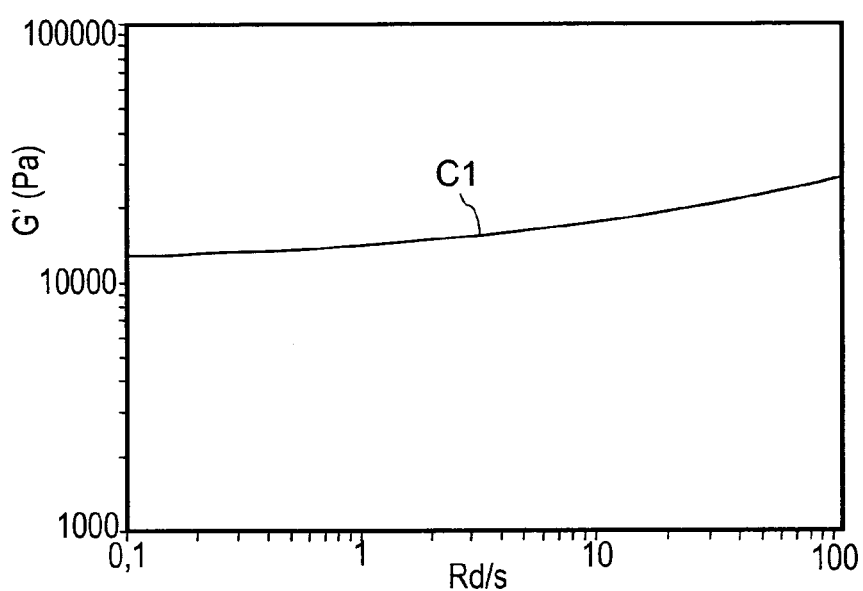
FIGS. 4 to 6 are graphical representations indicating the variations in properties of a protective layer according to one preferred embodiment of the present invention.

FIG. 4 represents a curve C1 indicating the variation in the rigidity or elastic component (i.e., shear storage modulus) G' of the layer 20 at 35° C. according to a shearing rate. On the curve C1, the rigidity of the layer 20 increases by about 11,000 to 20,000 Pa when the shearing rate changes from 0 to 100 rad/s.

Figure 5:
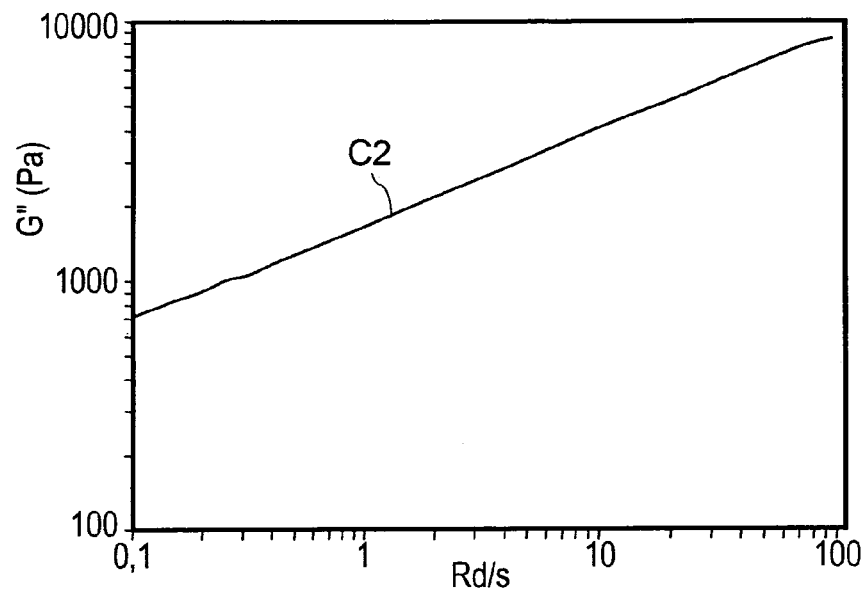

FIG. 5 represents a curve C2 indicating the variation in the viscous or resiliency component (i.e., shear loss modulus) G' of the layer 20 at 35° C. according to the shearing rate. On the curve C2, the viscosity of the layer 20 increases by about 700 to 8,000 Pa when the shearing rate changes from 0 to 100 rad/s.

Figure 6:
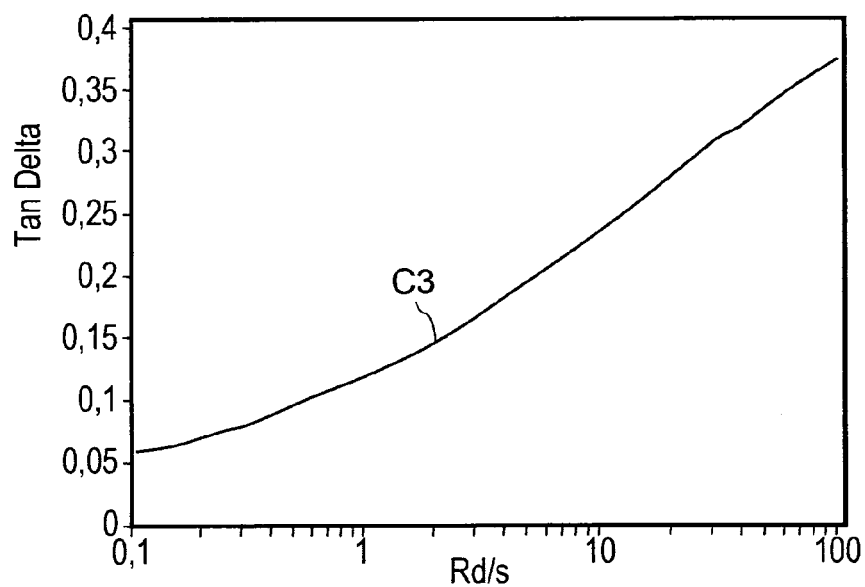

FIG. 6 represents a curve C3 indicating the variation in the resiliency factor (ratio between the dissipated energy and restored energy) or Tan delta of the layer 20 at 35° C. according to the shearing rate. On the curve C3, the Tan delta of the layer 20 increases by about 0.06 to 0.38 when the shearing rate changes from 0 to 100 radians/second.

The properties of the protective layer 20 are summarized in Table 2 below:

TABLE 2

| | |
|---|---|
| Rigidity or elastic component at 35° C. for a shearing rate between 0 and 100 rad/s | Approx. 11,000 to 20,000 Pa |
| Viscous or resiliency component at 35° C. for a shearing rate between 0 and 100 rad/s | Approx. 700 to 8,000 Pa |
| Resiliency factor at 35° C. for a shearing rate between 0 and 100 rad/s | Approx. 0.06 to 0.38 |
| Adhesiveness (tack) (g/cm$^2$) | Approx. 100 to 115 |

The protective layer 20 achieves a good compromise between a soft material to ensure maximum resiliency, and conversely, a hard material to ensure good resistance to shear stress and good distribution of the bearing stress. For this purpose, the thickness of the layer 20 can be between 1 and 4 mm.

The surface of the protective layer put in contact with the skin may not be smooth for better adhesiveness with the skin, with asperities the diameter of which is between 2 and 20 μm. Such a surface state can be obtained by polymerization free from any pressure against a smooth surface.

Figure 1:
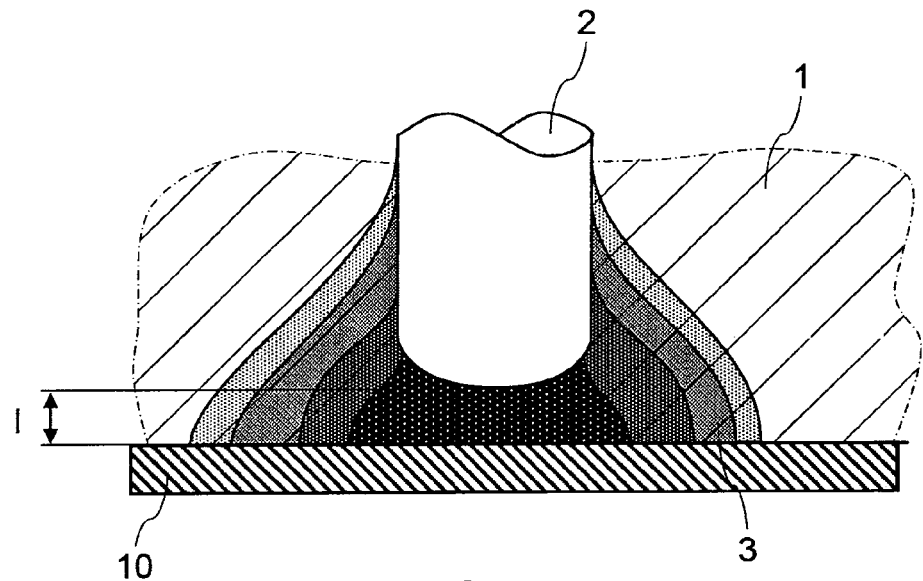
FIGS. 1 and 2 are schematic cross-sections an area of skin and tissues around a bone.
Figure 2:
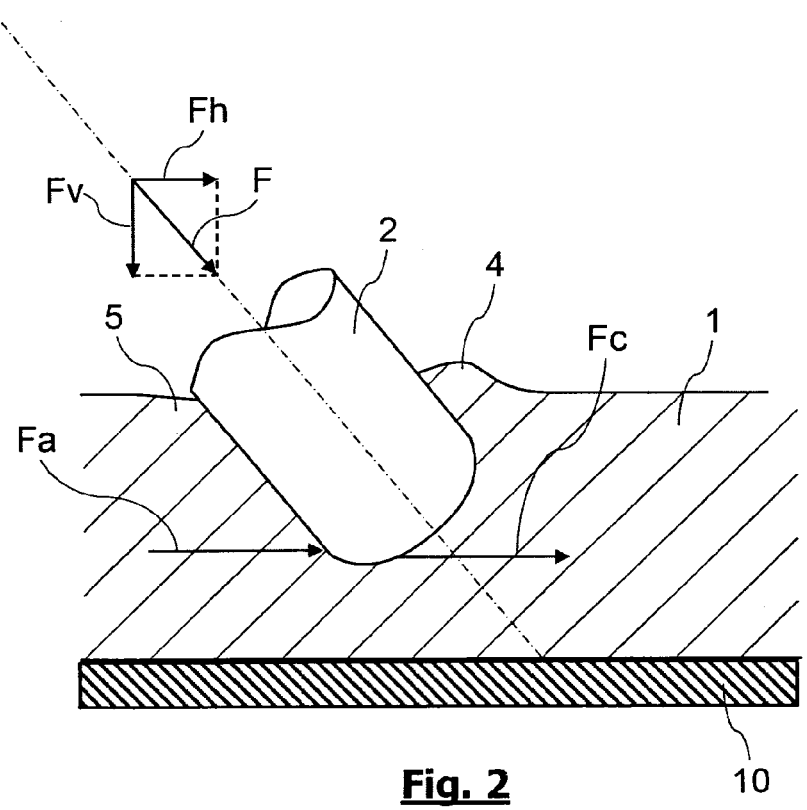

It can be seen, as represented in FIG. 3, that a part of the compression stresses is absorbed by the protective layer 20. Indeed, if FIGS. 2 and 3 are compared, the protective layer 20 is deformed and the thickness of the tissues under the bone is greater in FIG. 3. The result is that the compression stresses 6 are partly absorbed by the protective layer 20. Furthermore, a part of the shear stresses 7 is also absorbed by the layer 20. The result is a decrease in the repeated dynamic loading of the skin and of the deeper tissues, which causes fatigue and may result in lesions. This also results in preserving the vessels and thus maintaining the irrigation of the tissues. The significant adhesiveness of the layer 20 enables the friction between the skin and its environment to be significantly limited.

The protective layer 20 can be associated with a means holding it on the area of the skin to be protected. This means can be a piece of fabric or another more adhesive silicone gel fixed along the edges of the layer 20.

The epidermis has a large number of mechanico-sensitive receptors (mechanoreceptors) specialized for three types of sensations: pressure, vibration and so-called fine "touch" sensitivity, the main purpose of which is to protect. There is a reflex implementing mechanoreceptors of the epidermis, sensitive to pressure, the nervous system and the vasodilatation of the skin blood capillaries. The result is that the appearance of skin lesions and, in particular of bedsores, results from a disturbance of this reflex. Indeed, in the absence of vasodilatation of the skin blood capillaries compensating for pressure exerted on the skin, the capillaries are crushed. The skin tissues are then not sufficiently irrigated, which can cause the appearance of a so-called "inside-to-out" wound corresponding to a bedsore or a pressure ulcer.

The effect of the protective layer 20 described above, when it is applied directly onto the skin at a location undergoing local pressure, is that the layer 20 restores the vasodilatation reflex of the skin blood capillaries, induced by applying local pressure, or even improves this vasodilatation, particularly in diabetic people. This results in good skin blood circulation, even in the presence of pressure, preventing the formation of bedsores.

The protective layer also limits the risks of inhibiting this vasodilatation reflex by pain. It improves the distribution of load and contributes to absorbing the shear stress. It restores the quality of the skin, rendering it less sensitive to the deleterious effects of friction and/or pressure, thanks to its high ability to moisturize the skin.

It will be understood by those skilled in the art that various alternative embodiments and various applications of the present invention are possible. In particular, the present invention is not limited to a silicone gel obtained by polymerizing the mixtures previously described. It also covers any composition having the rigidity, viscosity and resiliency factor properties mentioned in Table 2. In this respect, it shall be noted that the protective layer can have an adhesiveness lower than that mentioned in Table 2, with the possibility of the protective layer being held on the skin by other means. The protective layer may also have a higher adhesiveness, while avoiding it being excessive to prevent the risk of lesions forming when the protective layer is removed from the skin.

The present invention does not apply solely to the prevention of bedsores. Indeed, the protective layer having the properties described above can be used to prevent any other lesion which may form on or in the epidermis.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for manufacturing a protective layer for protecting skin and tissues in a vicinity of the skin, the method comprising the steps of:

forming a mixture comprising approximately 15 wt. % of dimethyl-vinyl-terminated polydimethylsiloxane with a viscosity greater than 20,000 mPa·s at 20-25° C., approximately 25 wt. % of dimethyl-vinyl-terminated polydimethylsiloxane with a viscosity between 200 and 20,000 mPa·s at 20-25° C., approximately 45 wt. % of trimethyl-terminated polydimethylsiloxane, approximately 12 wt. % of trimethylsiloxy-treated pyrogenic silica, and approximately 3 wt. % of dimethyl-hydrogen-terminated co-polydimethylsiloxane-polymethyl-hydrogen-siloxane;

polymerizing at least partially the mixture to obtain a polymer gel; and forming the protective layer using the polymer gel, the polymer gel having, at a temperature of 35° C. and when a shearing rate varies between 0 and 100 radians/second,
a shear storage modulus or elastic component varying from 11,000 to 20,000 Pa,
a shear loss modulus or viscous component varying from 700 to 8,000 Pa, and
a Tan Delta varying from 0.06 to 0.38.

2. The method according to claim 1, wherein the protective layer has an adhesiveness between 100 and 115 g/cm$^2$.

3. The method according to claim 1, wherein the protective layer has a thickness between 1 and 4 mm.

4. The method according to claim 1, wherein the protective layer has a face comprising asperities having a diameter between 2 and 20 μm.

5. The method according to claim 1, wherein the approximately 45 wt. % of trimethyl-terminated polydimethylsiloxane has about $\frac{5}{6}^{ths}$ of trimethyl-terminated polydimethylsiloxane with a viscosity lower than 100 mPa·s at 20-25° C. and about $\frac{1}{6}^{ths}$ of trimethyl-terminated polydimethylsiloxane with a viscosity greater than 20,000 mPa·s at 20-25° C.

6. The method according to claim 1, wherein the polymerization is performed in the presence of platinum vinylsiloxane complex.

7. A protective layer for protecting skin and tissues in a vicinity of the skin, the protective layer being formed by polymerizing at least partially a mixture to obtain a polymer gel, the mixture comprising:

approximately 15 wt. % of dimethyl-vinyl-terminated polydimethylsiloxane with a viscosity greater than 20,000 mPa·s at 20-25° C., approximately 25 wt. % of dimethyl-vinyl-terminated polydimethylsiloxane with a viscosity between 200 and 20,000 mPa·s at 20-25° C., approximately 45 wt. % of trimethyl-terminated polydimethylsiloxane, approximately 12 wt. % of trimethylsiloxy-treated pyrogenic silica, and approximately 3 wt. % of dimethyl-hydrogen terminated co-polydimethylsiloxane-polymethyl-hydrogen-siloxane, the polymer gel having, at a temperature of 35° C. and when a shearing rate varies between 0 and 100 radians/second,
a shear storage modulus or elastic component varying from 11,000 to 20,000 Pa,
a shear loss modulus or viscous component varying from 700 to 8,000 Pa, and
a Tan Delta varying from approximately 0.06 to 0.38.

8. The protective layer according to claim 7, wherein the protective layer has an adhesiveness between 100 and 115 g/cm$^2$.

9. The protective layer according to claim 7, wherein the protective layer has a thickness between 2 and 3 mm.

10. The protective layer according to claim 7 further comprising a face having asperities, the diameter of the asperities being between 2 and 20 μm.

11. The protective layer according to claim 7, wherein the 45 wt. % of trimethyl-terminated polydimethylsiloxane comprises about $5/9^{ths}$ of trimethyl-terminated polydimethylsiloxane with a viscosity lower than 100 mPa·s at 20-25° C. and about $4/9^{ths}$ ths of trimethyl-terminated polydimethylsiloxane with a viscosity greater than 20,000 mPa·s at 20-25° C.

12. The protective layer according to claim 7, wherein the polymerization is performed in the presence of platinum vinylsiloxane complex.

13. A product for restoring or strengthening the vasodilatation reflex of skin blood capillaries, induced by applying local pressure, the product comprising a protective layer according to claim 7.

\* \* \* \* \*